US010618982B2

(12) United States Patent
Stucchi et al.

(10) Patent No.: US 10,618,982 B2
(45) Date of Patent: Apr. 14, 2020

(54) PROCESS IN WATER FOR THE PREPARATION OF BUTYRIC ESTERS OF HYALURONIC ACID SODIUM SALT

(71) Applicant: Sigea S.R.L., Trieste (IT)

(72) Inventors: Luca Stucchi, Frazione Tissano (IT); Rita Gianni, Monrupino (IT); Alessandra Sechi, Trieste (IT)

(73) Assignee: BMG PHARMA S.P.A., Milan (IT)

(*) Notice: Subject to any disclaimer, the term of this patent is extended or adjusted under 35 U.S.C. 154(b) by 172 days.

(21) Appl. No.: 15/542,443

(22) PCT Filed: Jan. 8, 2016

(86) PCT No.: PCT/EP2016/050268
§ 371 (c)(1),
(2) Date: Jul. 10, 2017

(87) PCT Pub. No.: WO2016/113192
PCT Pub. Date: Jul. 21, 2016

(65) Prior Publication Data
US 2018/0273648 A1    Sep. 27, 2018

(30) Foreign Application Priority Data

Jan. 13, 2015   (IT) .............. MI2015A0017

(51) Int. Cl.
C08B 37/08     (2006.01)
C08L 5/08      (2006.01)
A61K 31/728    (2006.01)
A61K 8/73      (2006.01)
A61Q 19/08     (2006.01)
A61K 9/00      (2006.01)
A61Q 19/00     (2006.01)
A61L 31/04     (2006.01)
A61L 27/20     (2006.01)

(52) U.S. Cl.
CPC .......... C08B 37/0072 (2013.01); A61K 8/735 (2013.01); A61K 9/0014 (2013.01); A61K 31/728 (2013.01); A61L 27/20 (2013.01); A61L 31/042 (2013.01); A61Q 19/00 (2013.01); A61Q 19/08 (2013.01); C08L 5/08 (2013.01); A61L 2430/34 (2013.01)

(58) Field of Classification Search
CPC ......... C08B 37/0072; C08L 5/08; A61K 8/73; A61K 31/728

USPC ...................................... 536/123.1
See application file for complete search history.

(56) References Cited

U.S. PATENT DOCUMENTS 5,874,417 A    2/1999    Prestwich et al.

FOREIGN PATENT DOCUMENTS

| CA | 1268404 A | 5/1990 | |
|----|-----------|--------|----|
| EP | 0416250 A2 | 3/1991 | |
| EP | 0941253 A1 | 9/1999 | |
| WO | 2004063364 A1 | 7/2004 | |
| WO | 2005092929 A1 | 10/2005 | |
| WO | 2009068215 A1 | 6/2009 | |
| WO | WO 2009/068215 A1 * | 6/2009 | ............. C08B 37/00 |
| WO | 2014064642 A1 | 5/2014 | |

OTHER PUBLICATIONS

Picotti et al, Carbohydrate Polymers, 2013, 93, 273-278.*
Coradini D. et al., "Hyaluronic acid as drug delivery for sodium butyrate: improvement of the anti-proliferative activity on a breast-cancer cell line", International Journal of Cancer, vol. 81, No. 3, May 5, 1999, pp. 411-416.
Coradini D. et al., "Hyaluronic-acid butyric esters as promising anti-neoplastic agents in human lung carcinoma: a preclinical study", Investigational New Drugs; The Journal of New Anti-Cancer Agents, vol. 22, No. 3, Aug. 1, 2004, pp. 207-217.
International Preliminary Report on Patentability of PCT/EP2016/050268 dated Sep. 12, 2016 and response filed on Nov. 3, 2016.
Piccotti F. et al., "Hyaluronic acid lipoate: synthesis and physicochemical properties", Carbohydrate Polymers vol. 93, No. 1, Apr. 12, 2012, pp. 273-278.
Search Report and Written Opinion of PCT/EP2015/050268 dated Mar. 31, 2016.

* cited by examiner

Primary Examiner — Ganapathy Krishnan
(74) Attorney, Agent, or Firm — Silvia Salvadori, P.C.; Silvia Salvadori

(57) ABSTRACT

The present invention relates to a process for the preparation of hyaluronic acid butyrate, or a salt thereof, acceptable for pharmaceutical or cosmetic use or as a medical device, comprising reacting hyaluronic acid, salified with sodium or another alkali metal, in aqueous solution with butyryl-imidazolide in the presence of sodium carbonate. The present invention also relates to pharmaceutical formulations, cosmetic formulations or medical devices containing the hyaluronic acid sodium salt (HA) butyric esters produced by said process.

8 Claims, 2 Drawing Sheets

PROCESS IN WATER FOR THE PREPARATION OF BUTYRIC ESTERS OF HYALURONIC ACID SODIUM SALT

This application is a U.S. national stage of PCT/EP2016/050268 filed on 8 Jan. 2016, which claims priority to and the benefit of Italian Application No. MI2015A000017 filed on 13 Jan. 2015, the contents of which are incorporated herein by reference in their entireties.

The present invention relates to a process for the preparation of butyric esters of hyaluronic acid sodium salt (HA) and to pharmaceutical formulations, cosmetic formulations or medical devices containing butyric esters of hyaluronic acid sodium salt (HA) produced by said process.

The present invention describes the process for preparing butyric esters of hyaluronic acid sodium salt (HA) by synthesis in an aqueous environment that surprisingly produces high degrees of substitution (DS) in butyric ester and preserves the polysaccharide chain of native hyaluronic acid against molecular degradation. The butyric esters of hyaluronic acid prepared by said process are free of impurities that are not tolerated and/or prohibited in the cosmetic field, possess anti-inflammatory and anti-irritant properties, and can therefore be advantageously used in the pharmaceutical and dermocosmetic field and in medical devices.

STATE OF THE ART

Hyaluronic acid butyrate (HABut), wherein the hydroxyl groups of hyaluronic acid are esterified with butyric acid residues having different degrees of substitution, is known to have anti-inflammatory, anti-proliferative and dermoprotective properties as a skin elasticiser and moisturiser.

Hyaluronic acid and the salts thereof are highly liable to degradation of the molecular weight by hydrolysis of the glycoside bonds of the polysaccharide chain. It is known from the literature that said hydrolysis is significantly influenced by pH, ionic strength and temperature conditions.

The derivatisation conditions of HA are therefore crucial to preserve the length of the polysaccharide chain. The ideal conditions are those which minimise the presence of water in the reaction medium and involve temperatures that are not very high and a pH close to neutrality, between 5 and 8.

EP 0941253 describes the preparation of butyric esters of hyaluronic acid having a low degree of substitution (max DS=0.25) with butyric anhydride in aprotic organic solvents such as N,N-dimethylformamide and dimethylsulphoxide (DMF, DMSO) in the presence of basic activators such as pyridine and N,N-dimethylaminopyridine (DMAP). The process of solubilisation in organic solvent involves the preparation of hyaluronic acid collidinium salt, obtained by preparing the acid form of the polysaccharide by acidifying the aqueous polysaccharide solution with 2N HCl and evaporating the solvent with a rotary evaporator, a process that causes the degradation of the molecular weight of HA.

WO 2005/092929 describes the preparation of hyaluronic acid butyric esters with a low degree of substitution (DS≤0.1). The synthesis, under homogenous conditions, involves preparing hyaluronic acid tetrabutylammonium (TBA) salt, soluble in aprotic organic solvents, by passing it through an ion-exchange column using a strong cation-exchange resin (Amberlite IR-120-plus), which said passage causes the degradation of the molecular weight.

WO2009/068215 describes the preparation of mixed butyric-formic esters of hyaluronic acid and their use in dermocosmetics, with dermoprotective and anti-inflammatory activities. The mixed esters are prepared with butyric anhydride in formamide (FA), with a basic DMAP activator.

The processes described use aprotic and protic organic solvents such as N,N dimethylformamide, formamide or dimethylsulphoxide, which are listed among the substances prohibited in cosmetic formulations according to Regulation (EC) no. 1223/2009. Organic bases are also used, such as N,N dimethylaminopyridine, which possess characteristics of high toxicity (LD50 of tens of ppm). The residues of the solvents, reagents and activators cannot be eliminated quantitatively during the purification process.

Reactions in water for the derivatisation of hyaluronic acid are reported in EP0416250, which reports the formation of N-acylurea and O-isoacylurea on the carboxyl group of hyaluronic acid due to the reaction with carbodiimides or bis-carbodiimides. The reaction takes place in water, at a controlled pH which does not degrade the polysaccharide.

U.S. Pat. No. 5,874,417 describes the functionalisation of the carboxyl of hyaluronic acid with a hydrazide in water under mild conditions.

A. Mero et al. (*Polymer* 2014, 6, 346-369) reports that HA can be derivatised in water. However, in aqueous phase, many reactions need to be conducted under acid or alkaline conditions involving significant degradation of the HA chain. The article reports reactions in water with carbodiimides leading to the formation of amido bonds on the carboxyl groups.

The process according to the present invention also produces HABut with high degrees of substitution, only using water as solvent and sodium carbonate as basic activator. The product obtained does not present any solvent or basic activator residues which would give rise to particular safety problems.

DESCRIPTION OF THE INVENTION

Figure 1:
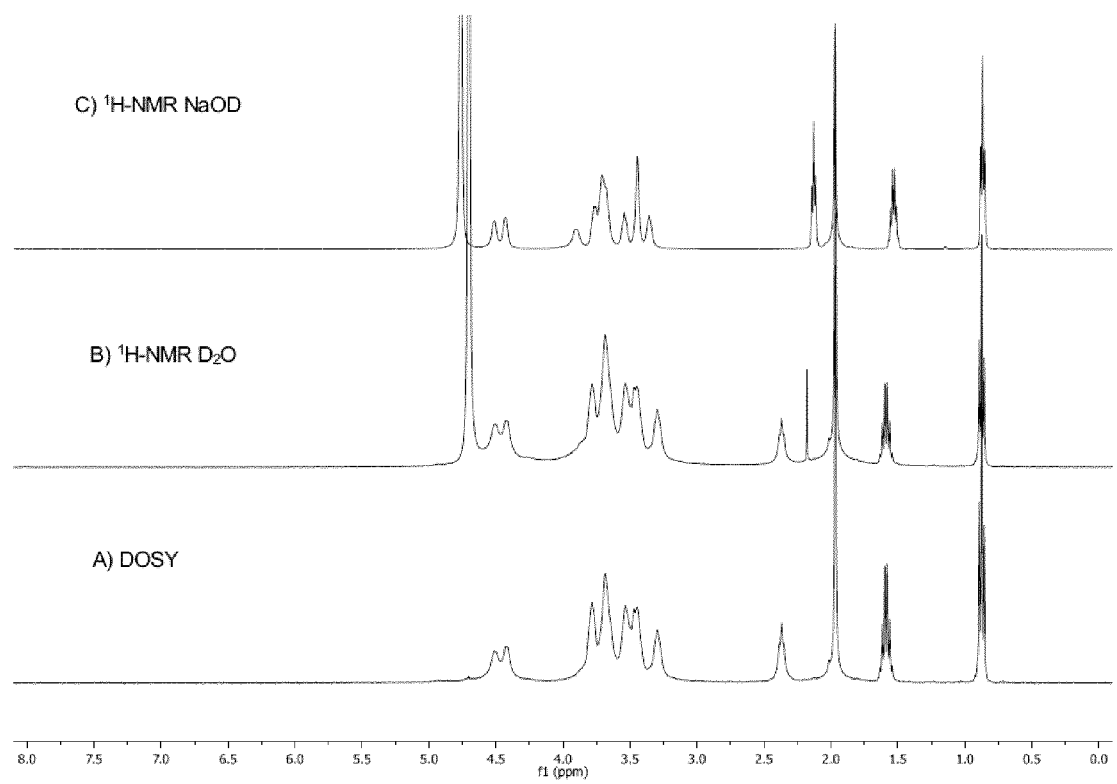
FIG. 1 shows NMR spectra of: (a) a product obtained by applying a DOSY sequence that only retains the signals attributable to chemical groups covalently bonded to the polymer; (b) a product obtained before and (c) after the hydrolysis of the butyric ester by addition of deuterated sodium hydroxide (NaOD).

The present invention relates to a process for the preparation of hyaluronic acid butyrate, or a salt thereof, acceptable for pharmaceutical or cosmetic use or as a medical device, comprising reacting hyaluronic acid, preferably salified with sodium or another alkali metal, in aqueous solution with butyryl-imidazolide in the presence of sodium carbonate.

The process according to the invention is preferably used to prepare hyaluronic acid butyrate sodium salt.

The hyaluronic acid sodium salt used in the process preferably has a weight-average molecular weight (MW) ranging between $10^3$ and $10^6$ Daltons.

The hyaluronic acid salt is dissolved in demineralised water, and sodium carbonate, followed by butyryl-imidazolide, is added to the resulting solution.

The reaction mixture is maintained at a temperature ranging between 20° C. and 30° C. for not less than 60 minutes.

The pH of the reaction ranges between pH 11 and 9.

When the reaction is complete, the mixture is adjusted to a neutral pH, and the product is recovered by precipitation in a suitable solvent. The product thus obtained is then purified, for example by successive washes with suitable solvents and filtration.

The process according to the invention produces hyaluronic acid butyrate with different degrees of substitution. The degree of substitution (DS), defined as the ratio between the number of butyric acid residues per GlcNAc-GlcUA disaccharide unit of hyaluronic acid, can range, for example, between 0.01 and 2.5.

Different degrees of substitution are obtained by varying the ratio between hyaluronic acid and butyryl-imidazolide.

The hyaluronic acid butyrate obtained by the process according to the invention does not contain solvent residues or toxic reagents and can be used in pharmaceutical formulations, cosmetic formulations and medical devices.

The subject of the present invention therefore includes pharmaceutical and cosmetic formulations containing hyaluronic acid butyrate, or a salt thereof, acceptable for pharmaceutical or cosmetic use, obtained by the process reported above, and at least one excipient and/or carrying agent acceptable for pharmaceutical or cosmetic use.

The hyaluronic acid butyrate obtained by the process reported, due to the absence of solvents and reagents prohibited by the legislation governing cosmetic ingredients, can be used in the dermocosmetic field for topical use with hydrating, elasticising, toning, anti-aging or anti-acne activity in formulations with a high safety profile which are suitable, for example, for hypoallergenic products or sensitive skin.

The molecule also possesses marked anti-irritant and anti-inflammatory activities greater than those of hyaluronic acid (HA) and sodium butyrate (NaBut), influencing the acute inflammatory response, as verified on an in vitro neutrophil model (polymorphonuclear leukocytes or PMN). As a result of said characteristic, the hyaluronic acid butyrate produced by the process described is applicable as active ingredient in pharmaceutical formulations, cosmetic formulations or medical devices as adjuvant in the treatment of skin lesions such as inflammations, ulcers, and lesions caused by hyperthermia induced by radiation such as UV rays, X rays and gamma rays.

EXAMPLES

Instrumentation Used:
Bruker Avance 400 MHz spectrometer equipped with a 5 mm multinuclear reverse probe with a z gradient for determination of the degree of substitution (DS);
Viscotek HP-SEC-TDA chromatograph model 270 max equipped with a triple detector (light scattering at 90° C. and 7° C., refractive index and viscometer) to determine the distribution of the molecular weights and the weight-average molecular weight (MW).
Determination of Degree of Substitution (DS)

The degree of substitution in butyrate esters on the hyaluronic acid derivative was quantitated by NMR spectroscopy. The $^1$H NMR spectra were effected in $D_2O$ with a Bruker Avance 400 MHz spectrometer equipped with a 5 mm multinuclear reverse probe with a z gradient. The tests were conducted by thermostating the measurement probe to 300° K.

The test includes Diffusion Ordered Spectroscopy (DOSY) analysis, which verifies the existence of the covalent bond between the polymer and butyric acid.

The quantitation of DS in butyrate ester is performed after exhaustive hydrolysis with NaOD directly in the NMR tube.

The $^1$H NMR spectrum of the hydrolysate allows integration of the signals attributable to butyric acid (vicinal methyl and methylene protons) and those attributable to hyaluronic acid (saccharide protons, excluding the two anomeric protons); their ratio determines the degree of substitution.

Methods

Determination of Distribution of Molecular Weight and Weight-Average Molecular Weight (MW) by HP-SEC-TDA Chromatography The samples were subjected to size-exclusion chromatography using a combination of three detectors (light scattering at 90° and 7°, refraction index and viscosimeter). Processing of the chromatogram allows the distribution of the molecular weights Mw (weight-average molecular weight) to be determined.

Chromatography Conditions
Instrumentation Viscotek 270 max.
Columns: A7000, A6000mx2, temperature 35° C.
Mobile phase: PBS.
Flow rate: 0.750 ml/min
Detector: Viscotek TDA equipped with refraction index, capillary viscosimeter and light scattering with measurement at 90° and 7°, temperature 35° C.
Volume injected: 100 μl.
Evaluation of Superoxide Anion Production The production of ROS, the indicator of metabolic activation of PMNs, was evaluated in terms of quantity of superoxide anion ($O_2^-$) released into the medium following activation of the neutrophils in the wells of microtitre plates coated with fibrinogen (FBG), collagen IV (CIV), HA or HABut. A spectrophotometric method was used to measure the quantity of cytochrome c reduced by the superoxide anion produced by the cells during incubation on the plate.

Evaluation of Adhesion to Biological Surfaces

Cell adhesion to the surface during the metabolic assay was evaluated by assaying the activity of the enzyme myeloperoxidase (MPO), a marker enzyme contained in the azurophilic granules of PMNs. A protocol described by Menegazzi et al. (*A new, one-step assay on whole cell suspensions for peroxidase secretion by human neutrophils and eosinophils*. Menegazzi R, Zabucchi G, Knowles A, Cramer R, Patriarca P. *J Leukoc Biol*. 1992 December; 52(6):619-24) was used. The myeloperoxidase activity was assayed with a quantitative colorimetric enzyme test that measures the oxidation of the 3,3',5,5'-tetramethylbenzidine (TMB) substrate by the MPO enzyme in the presence of $H_2O_2$.

Example 1: Synthesis of Hyaluronic Acid Sodium Salt Butyric Ester, DS=0.3 (BUT12103)

100 ml of demineralised water is introduced into a 1 l reactor, followed by 10.0 g of sodium hyaluronate with a MW of 280 kDa. The mixture is thermostated at 25° C. and maintained under stirring at a constant temperature until completely dissolved.

Disodium carbonate ($Na_2CO_3$—1.6 g) is then added, followed by butyryl-imidazolide (2.6 g) after 30 minutes' stirring. The solution is left under stirring for 1 hour at 25°, and the product is then isolated by precipitation in acetone and subsequent decanting.

The solution is purified by successive washes in acetone, and recovered by negative pressure filtration.

Finally the product is suspended in acetone, left under stirring for at least 30 minutes and then isolated, eliminating the solvent by filtration.

The precipitate is dried at room temperature for at least 3 h and then in a vacuum oven at a temperature of ≤60° C. for at least 16 hours.

10 mg of sample is solubilised in 0.7 ml of deuterated water ($D_2O$) and transferred to an NMR test tube.

The NMR spectra are reported in FIG. 1; the bottom spectrum (a) is obtained by applying a DOSY sequence that only retains the signals attributable to chemical groups covalently bonded to the polymer.

The other two $^1H$ NMR spectra are respectively before (b) and after (c) the hydrolysis of the butyric ester by addition of deuterated sodium hydroxide (NaOD). By integrating the signals of the $^1H$ NMR spectra, a DS of 0.30 is determined.

Example 2: Determination of Distribution of Molecular Weight and Weight-Average Molecular Weight (MW)

The hyaluronic acid sodium salt sample used for synthesis of the butyric ester described in Example 1, certified with a MW of 280 kDa, was analysed by HP-SEC-TDA chromatography. The distribution of the experimental molecular weights gives a weight-average molecular weight (MW) of 300 kDa.

The sample of hyaluronic acid sodium salt butyric ester produced as described in Example 1 was analysed by HP-SEC-TDA chromatography. The distribution of the experimental molecular weights gives a weight-average molecular weight (MW) of 360 kDa.

Example 3: Synthesis of Hyaluronic Acid Sodium Salt Butyric Ester, DS=0.3 (BUT14014)

1 l of demineralised water is poured into a 15 l reactor, followed by 100.0 g of sodium hyaluronate with a MW of 290 kDa. The mixture is thermostated at 25° C. and maintained under stirring at a constant temperature until completely dissolved.

Disodium carbonate ($Na_2CO_3$—15.9 g) is then added, followed by butyryl-imidazolide (25.9 g) after 30 minutes' stirring. The solution is left under stirring for 1 hour at 25° C.; the reaction is then quenched by adding an aqueous solution consisting of hydrochloric acid (HCl) and sodium chloride (NaCl).

The solution is left under stirring for at least 30 minutes, and the product is then recovered by precipitation in isopropanol.

When precipitation has finished, the solution is left under stirring for at least 16 hours; the mixture is transferred and the product isolated by filtration.

The product is then purified by successive washes in isopropanol, after which the product is recovered by filtration.

Finally, the product is suspended in isopropanol, left under stirring for at least 30 minutes and then isolated, eliminating the solvent by filtration.

The precipitate is dried at room temperature for at least 3 h and then in a vacuum oven at a temperature of ≤60° C. for at least 16 hours.

10 mg of sample is solubilised in 0.7 ml of $D_2O$ and transferred to an NMR test tube.

10 mg of sample is solubilised in 0.7 ml of NaOD and transferred to an NMR test tube.

By integrating the signals of the $^1H$ NMR spectra, a DS of 0.30 is determined.

Example 4: Synthesis of Hyaluronic Acid Sodium Salt Butyric Ester, DS=0.3 (HBint05012014)

2.5 l of demineralised water is introduced into a 15 l reactor, followed by 250.0 g of sodium hyaluronate with a MW of 290 kDa. The mixture is thermostated at 25° C. and maintained under stirring at a constant temperature until completely dissolved.

Disodium carbonate ($Na_2CO_3$—39.8 g) is then added, followed by butyryl-imidazolide (64.8 g) after 30 minutes' stirring. The solution is left under stirring for 1 hour at 25° C., and the reaction is then quenched by adding an aqueous solution consisting of HCl and NaCl.

The solution is left under stirring for at least 30 minutes, and the product is then recovered by precipitation in acetone.

When precipitation has finished, the solution is left under stirring for at least 30 minutes. The product is then isolated by decanting.

The product is then purified by successive washes in acetone, after which the product is recovered by filtration.

Finally, the product is suspended in acetone, left under stirring for at least 30 minutes and then isolated, eliminating the solvent by filtration.

The precipitate is dried at room temperature for at least 16 h and then under vacuum at a temperature of ≤60° C. for at least 24 hours.

10 mg of sample is solubilised in 0.7 ml of $D_2O$ and transferred to an NMR test tube.

10 mg of sample is solubilised in 0.7 ml of NaOD and transferred to an NMR test tube.

By integrating the signals of the $^1H$ NMR spectra, a DS of 0.30 is determined.

Example 5: Synthesis of Hyaluronic Acid Sodium Salt Butyric Ester, DS=0.58 (BUT14017)

100 ml of demineralised water is introduced into a 1 l reactor, followed by 10.0 g of sodium hyaluronate with a MW of 290 kDa. The mixture is thermostated at 25° C. and maintained under stirring at a constant temperature until completely dissolved.

Disodium carbonate ($Na_2CO_3$—2.6 g) is then added, followed by butyryl-imidazolide (9.2 g) after 30 minutes' stirring. The solution is left under stirring for 1 hour at 25° C., and the reaction is then quenched by adding an aqueous solution consisting of HCl and NaCl.

The solution is left under stirring for at least 30 minutes, and the product is then recovered by precipitation in isopropanol. The product is then isolated by decanting.

The product is then purified by successive washes in isopropanol, after which the product is recovered by filtration.

Finally, the product is suspended in isopropanol, left under stirring for at least 30 minutes and then isolated, eliminating the solvent by filtration.

The precipitate is dried at room temperature for at least 3 h and then under vacuum at a temperature of ≤60° C. for at least 24 hours.

10 mg of sample is solubilised in 0.7 ml of $D_2O$ and transferred to an NMR test tube.

10 mg of sample is solubilised in 0.7 ml of NaOD and transferred to an NMR test tube.

By integrating the signals of the $^1H$ NMR spectra, a DS of 0.58 is determined.

Example 6: Synthesis of Hyaluronic Acid Sodium Salt Butyric Ester, DS=0.85 (BUT14019)

100 ml of demineralised water is introduced into a 1 l reactor, followed by 10.0 g of sodium hyaluronate with a MW of 290 kDa. The mixture is thermostated at 25° C. and maintained under stirring at a constant temperature until completely dissolved.

Disodium carbonate ($Na_2CO_3$—5.3 g) is then added, followed by butyryl-imidazolide (9.2 g) after 30 minutes' stirring. The solution is left under stirring for 1 hour at 25° C., and the reaction is then quenched by adding an aqueous solution of HCl and NaCl.

The solution is left under stirring for at least 30 minutes, and the product is then recovered by precipitation in isopropanol. The product is then isolated by decanting.

The product is then purified by successive washes in isopropanol, after which the product is recovered by filtration.

Finally, the product is suspended in isopropanol, left under stirring for at least 30 minutes and then isolated, eliminating the solvent by filtration.

The precipitate is dried at room temperature for at least 3 h and then under vacuum at a temperature of ≤60° C. for at least 24 hours.

10 mg of sample is solubilised in 0.7 ml of $D_2O$ and transferred to an NMR test tube.

10 mg of sample is solubilised in 0.7 ml of NaOD and transferred to an NMR test tube.

By integrating the signals of the $^1H$ NMR spectra, a DS of 0.85 is determined.

Example 7: Synthesis of Hyaluronic Acid Sodium Salt Butyric Ester, DS=1.30 (HBint04042014-BUT14023)

100 ml of demineralised water is introduced into a 1 l reactor, followed by 10.0 g of sodium hyaluronate with a MW of 290 kDa. The mixture is thermostated at 25° C. and maintained under stirring at a constant temperature until completely dissolved.

Disodium carbonate ($Na_2CO_3$—13.2 g) is then added, followed by butyryl-imidazolide (23.1 g) after 30 minutes' stirring. The solution is left under stirring for 1 hour at 25° C., and the reaction is then quenched by adding an aqueous solution of HCl.

The solution is left under stirring for at least 30 minutes, and the product is then recovered by precipitation in isopropanol. The product is then isolated by decanting.

The product is then purified by successive washes in isopropanol, after which the product is recovered by filtration.

Finally, the product is suspended in isopropanol, left under stirring for at least 30 minutes and then isolated, eliminating the solvent by filtration.

The precipitate is dried in an airstream at room temperature for at least 3 h and then under vacuum at a temperature of ≤60° C. for at least 24 hours.

10 mg of sample is solubilised in 0.7 ml of D2O and transferred to an NMR test tube.

10 mg of sample is solubilised in 0.7 ml of NaOD and transferred to an NMR test tube.

By integrating the signals of the $^1H$ NMR spectra, a DS of 1.30 is determined.

Example 8: Synthesis of High-Molecular-Weight Hyaluronic Acid Sodium Salt Butyric Ester, DS=0.24 (HBint01042014-BUT14025)

1 l of demineralised water is poured into a 5 l reactor, followed by 50.0 g of sodium hyaluronate with a MW of 1270 kDa. The mixture is thermostated at 25° C. and maintained under stirring at a constant temperature until completely dissolved.

Disodium carbonate ($Na_2CO_3$—10.6 g) is then added, followed by butyryl-imidazolide (25.9 g) after 90 minutes' stirring. The solution is left under stirring for 1 hour at 25° C., and the reaction is then quenched by adding 360 ml of an aqueous solution consisting of HCl and NaCl.

The solution is left under stirring for at least 30 minutes, and the product is then recovered by precipitation in acetone. When precipitation has finished, the solution is left under stirring for at least 16 hours. The product is then isolated by decanting.

The product is then purified by successive washes in acetone, after which the product is recovered by filtration.

Finally, the product is suspended in acetone, left under stirring for at least 30 minutes and then isolated, eliminating the solvent by filtration.

The precipitate is dried at room temperature for at least 16 h and then under vacuum at a temperature of ≤60° C. for at least 24 hours.

3 mg of solid is solubilised in 0.7 mL of D2O and transferred to an NMR tube.

10 mg of solid is solubilised in 0.7 mL of NaOD and transferred to an NMR tube.

By integrating the signals of the $^1H$ NMR spectra, a DS of 0.24 is determined.

Example 9: Synthesis of High-Molecular-Weight Hyaluronic Acid Sodium Salt Butyric Ester, DS=0.51 (HBint03042014-BUT14032)

0.72 l of demineralised water is introduced into a 5 l reactor, followed by 30.0 g of sodium hyaluronate with a MW of 1270 kDa. The mixture is thermostated at 25° C. and maintained under stirring at a constant temperature until completely dissolved.

Disodium carbonate ($Na_2CO_3$—23.8 g) is then added, followed by butyryl-imidazolide (60.9 g) after 60 minutes' stirring. The solution is left under stirring for 1 hour at 25° C., and the reaction is then quenched by adding an aqueous solution of HCl.

The solution is left under stirring for at least 30 minutes, and the product is then recovered by precipitation in acetone. When precipitation has finished, the solution is left under stirring for at least 16 hours. The product is then isolated by decanting.

The product is then purified by successive washes in acetone, after which the product is recovered by filtration.

Finally, the product is suspended in acetone, left under stirring for at least 30 minutes and then isolated, eliminating the solvent by filtration.

The precipitate is dried at room temperature for at least 30 h and then under vacuum at a temperature of ≤60° C. for at least 24 hours.

3 mg of sample is solubilised in 0.7 ml of $D_2O$ and transferred to an NMR test tube.

10 mg of sample is solubilised in 0.7 ml of NaOD and transferred to an NMR test tube.

By integrating the signals of the $^1H$ NMR spectra, a DS of 0.51 is determined.

Example 10: Synthesis of High-Molecular-Weight Hyaluronic Acid Sodium Salt Butyric Ester, DS=0.97 (HBint02042014-BUT14031)

0.85 l of demineralised water is introduced into a 5 l reactor, followed by 30.0 g of sodium hyaluronate with a MW of 1270 kDa. The mixture is thermostated at 25° C. and maintained under stirring at a constant temperature until completely dissolved.

Disodium carbonate ($Na_2CO_3$—47.6 g) is then added, followed by butyryl-imidazolide (138.3 g) after 60 minutes' stirring. The solution is left under stirring for 1 hour at 25° C., and the reaction is then quenched by adding an aqueous solution of HCl.

The solution is left under stirring for at least 30 minutes, and the product is then recovered by precipitation in acetone. When precipitation has finished, the solution is left under stirring for at least 16 hours, and the product is isolated by filtration.

The product is then purified by successive washes in acetone, after which the product is recovered by filtration.

Finally, the product is suspended in acetone, left under stirring for at least 30 minutes and then isolated, eliminating the solvent by filtration.

The precipitate is dried at room temperature for at least 16 h and then under vacuum at a temperature of ≤60° C. for at least 24 hours.

3 mg of sample is solubilised in 0.7 ml of $D_2O$ and transferred to an NMR test tube.

10 mg of sample is solubilised in 0.7 ml of NaOD and transferred to an NMR test tube.

By integrating the signals of the $^1H$ NMR spectra, a DS of 0.97 is determined.

Example 11: Synthesis of Low-Molecular-Weight Hyaluronic Acid Sodium Salt Butyric Ester, DS=0.46 (BUT14037)

35 ml of demineralised water is poured into an 0.5 l flask, followed by 5.0 g of sodium hyaluronate with a MW of 45 kDa. The mixture is thermostated at 25° C. and maintained under stirring at a constant temperature until completely dissolved.

Disodium carbonate ($Na_2CO_3$—0.8 g) is then added, followed by butyryl-imidazolide (1.3 g) after 30 minutes' stirring. The solution is left under stirring for 1 hour at 25° C., and the reaction is then quenched by adding an aqueous solution of HCl and NaCl.

The solution is left under stirring for at least 30 minutes, and the product is then recovered by precipitation in isopropanol. When precipitation has finished, the solution is left under stirring for at least 16 hours; the mixture is transferred and the product isolated by filtration.

The product is then purified by successive washes in isopropanol, after which the product is recovered by filtration.

Finally, the product is suspended in isopropanol, left under stirring for at least 30 minutes and then isolated, eliminating the solvent by filtration.

The precipitate is dried at room temperature for at least 16 h and then under vacuum at a temperature of ≤60° C. for at least 16 hours.

10 mg of sample is solubilised in 0.7 ml of $D_2O$ and transferred to an NMR test tube.

10 mg of sample is solubilised in 0.7 ml of NaOD and transferred to an NMR test tube.

By integrating the signals of the $^1H$ NMR spectra, a DS of 0.46 is determined.

Example 12: Synthesis of Low-Molecular-Weight Hyaluronic Acid Sodium Salt Butyric Ester, DS=1.68 (BUT14039)

12.5 ml of demineralised water is introduced into an 0.25 l flask, followed by 5.0 g of sodium hyaluronate with a MW of 45 kDa. The mixture is thermostated at 25° C. and maintained under stirring at a constant temperature until completely dissolved.

Disodium carbonate ($Na_2CO_3$—6.6 g) is then added, followed by butyryl-imidazolide (11.9 g) after 30 minutes' stirring. The solution is left under stirring for 1 hour at 25° C., and the reaction is then quenched by adding an aqueous solution of HCl.

The solution is left under stirring for at least 30 minutes, and the product is then recovered by precipitation in isopropanol. When precipitation has finished, the solution is left under stirring for at least 16 hours. The product is then isolated by decanting.

The product is then purified by successive washes in isopropanol, after which the product is recovered by filtration.

The precipitate is dried at room temperature for at least 16 h and then under vacuum at a temperature of ≤60° C. for at least 16 hours.

10 mg of sample is solubilised in 0.7 ml of $D_2O$ and transferred to an NMR test tube.

10 mg of sample is solubilised in 0.7 ml of NaOD and transferred to an NMR test tube.

By integrating the signals of the $^1H$ NMR spectra, a DS of 1.68 is determined.

Example 13: Synthesis of Low-Molecular-Weight Hyaluronic Acid Sodium Salt Butyric Ester, DS=1.90 (BUT14042)

25.0 ml of demineralised water is poured into an 0.5 l flask, followed by 10.0 g of sodium hyaluronate with a MW of 45 kDa. The mixture is thermostated at 25° C. and maintained under stirring at a constant temperature until completely dissolved.

Disodium carbonate ($Na_2CO_3$—13.2 g) is then added, followed by butyryl-imidazolide (68.2 g) after 30 minutes' stirring. The solution is left under stirring for 2 hours at 25° C., and the reaction is then quenched by adding an aqueous solution of HCl.

The solution is left under stirring for at least 30 minutes, and the product is then recovered by precipitation in isopropanol. When precipitation has finished, the solution is left under stirring for at least 16 hours. The product is then isolated by decanting.

The product is then purified by successive washes in isopropanol, after which the product is recovered by filtration.

The precipitate is dried at room temperature for at least 16 h and then under vacuum at a temperature of ≤60° C. for at least 16 hours.

10 mg of sample is solubilised in 0.7 ml of $D_2O$ and transferred to an NMR test tube.

10 mg of sample is solubilised in 0.7 ml of NaOD and transferred to an NMR test tube.

By integrating the signals of the $^1H$ NMR spectra, a DS of 1.90 is determined.

Example 14: Synthesis of Low-Molecular-Weight Hyaluronic Acid Sodium Salt Butyric Ester, DS=0.06 (BUT14043)

50.0 ml of demineralised water is introduced into an 0.5 l flask, followed by 10.0 g of sodium hyaluronate with a MW of 45 kDa. The mixture is thermostated at 25° C. and maintained under stirring at a constant temperature until completely dissolved.

Disodium carbonate ($Na_2CO_3$—0.2 g) is then added, followed by butyryl-imidazolide (0.3 g) after 30 minutes' stirring. The solution is left under stirring for 2 hours at 25° C., and the reaction is then quenched by adding an aqueous solution of HCl.

The solution is left under stirring for at least 30 minutes, and the product is then recovered by precipitation in isopropanol. When precipitation has finished, the product is isolated by negative pressure filtration; the product is then purified by successive washes in isopropanol, after which the product is recovered by filtration.

The precipitate is dried at room temperature for at least 16 h and then under vacuum at a temperature of ≤60° C. for at least 7 hours.

10 mg of sample is solubilised in 0.7 ml of $D_2O$ and transferred to an NMR test tube.

10 mg of sample is solubilised in 0.7 ml of NaOD and transferred to an NMR test tube.

By integrating the signals of the $^1H$ NMR spectra, a DS of 0.06 is determined.

Example 15: Synthesis of Low-Molecular-Weight Hyaluronic Acid Sodium Salt Butyric Ester, DS=0.02 (BUT14044)

50.0 ml of demineralised water is introduced into an 0.5 l flask, followed by 10.0 g of sodium hyaluronate with a MW of 45 kDa. The mixture is thermostated at 25° C. and maintained under stirring at a constant temperature until completely dissolved.

Disodium carbonate ($Na_2CO_3$—0.1 g) is then added, followed by butyryl-imidazolide (0.1 g) after 30 minutes' stirring. The solution is left under stirring for 1 hour at 25° C., and the reaction is then quenched by adding an aqueous solution of HCl and NaCl.

The solution is left under stirring for at least 30 minutes, and the product is then recovered by precipitation in isopropanol. When precipitation has finished, the solution is left under stirring for at least 16 hours; the mixture is then transferred and the product isolated by filtration.

The product is then purified by successive washes in isopropanol, after which the product is recovered by filtration.

The precipitate is dried at room temperature for at least 16 h and then under vacuum at a temperature of ≤60° C. for at least 16 hours.

10 mg of sample is solubilised in 0.7 ml of $D_2O$ and transferred to an NMR test tube.

10 mg of sample is solubilised in 0.7 ml of NaOD and transferred to an NMR test tube.

By integrating the signals of the $^1H$ NMR spectra, a DS of 0.02 is determined.

Example 16: Production of Superoxide Anion by PMNs Activated by TNF

Production of superoxide anion by PMNs stimulated for 45 min with the proinflammatory cytokine TNF in wells coated with FBG (fibrinogen; surface permissive to PMN adhesion); CIV (type IV collagen—non-permissive surface); HA: hyaluronic acid; HABut: sodium hyaluronate butyrate DS=0.3 Example no. 4.

Wells coated with the various substrates are filled with an 0.18 mM solution of cytochrome c and 0.15 ng/ml TNF in Hepes buffer. The modules thus prepared are heated for 10 min at 37 degrees in a humidified incubator; a cell suspension of $1.5 \times 10^6$ PMN/ml in Hepes buffer is added to each well. At 15-minute intervals the plate is removed from the incubator and subjected to spectrophotometric analysis in a microplate reader at the wavelengths of 550 nm and 540 nm, which correspond respectively to the absorption peak of reduced cytochrome c and the isosbestic point of the absorption spectra of reduced and oxidised cytochrome c. The difference between the absorbance values recorded at the two wavelengths is proportional to the quantity of reduced cytochrome c. The quantity of $O_2^-$ produced by $10^6$ cells is calculated as follows:

$$\text{nmoles } O_2^-/10^6 PMN = OD \times 10^6/0.0037 \times n$$

wherein n is the number of cells added to each well.

Figure 2:
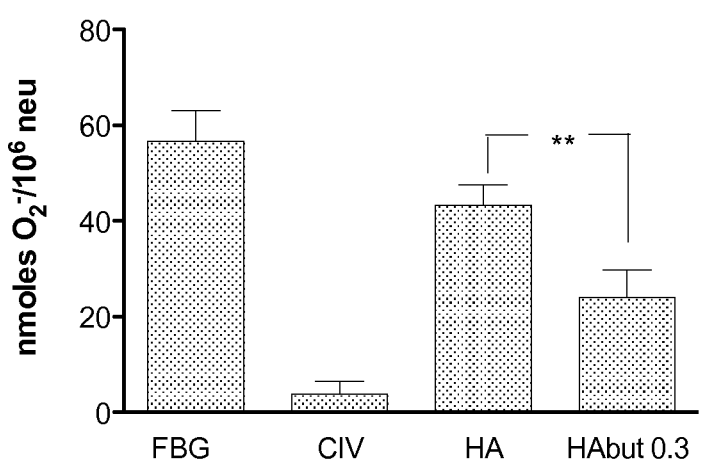
FIG. 2 shows a reduction in production of superoxide anion (p<0.001 calculated by Student's "t" test with n=4) in response to the TNF of the PMNs incubated on the surface coated with HABut.

The histogram reported in FIG. 2 shows a significant reduction in production of superoxide anion (p<0.001 calculated by Student's "t" test with n=4) in response to the TNF of the PMNs incubated on the surface coated with HABut, with a degree of substitution of 0.3 compared with those incubated on a surface with HA.

Example 17: Test of PMN Adhesion to Biological Surfaces

Adhesion of PMN to a surface coated with FBG (surface permissive to PMN adhesion); CIV (non-permissive surface); HA: hyaluronic acid; HABut: sodium hyaluronate butyrate DS=0.3 Example no. 4. Resting: PMN not activated with TNF. TNF: PMN activated with TNF; PMA: PMN activated with phorbol 12-myristate 13-acetate.

After taking the spectrophotometric readings for the measurement of $O_2^-$ production, the microplate wells are filled with PBS and centrifuged at 200 rpm for 5 minutes to remove the cells not adhering to the surface. The myeloperoxidase activity is assayed by measuring the oxidation of the 3',5,5'-tetramethylbenzidine (TMB) substrate by the MPO enzyme in the presence of $H_2O_2$. An acetate buffer containing TMB, cetyltrimethylammonium (CTAB) and 3-amino-1,2-4-triazole (AMT) is added to each well, and the plate is stirred for 5 min to facilitate cell lysis and promote the release of MPO from the granules. The activity of eosinophil peroxidase from the eosinophils which can contaminate the PMN preparation is inhibited with ATM. 2 minutes after the addition of $H_2O_2$ the reaction is quenched with $H_2SO_4$, and the absorbance of each well is measured at the wavelength of 405 nm. The percentage of adhering cells is calculated with reference to a standard curve constructed, in each experiment, on the basis of the peroxidase activity values calculated for known quantities of cells.

Figure 3:
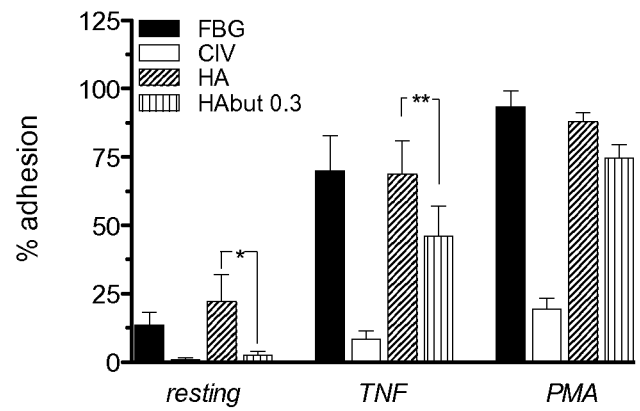
FIG. 3 shows a reduction (p<0.001 calculated by Student's "t" test with n=4) in the number of activated and non-activated PMNs adhering to the surface coated with HABut.

The histogram reported in FIG. 3 shows a significant reduction (p<0.001 calculated by Student's "t" test with n=4) in the number of activated and non-activated PMNs adhering to the surface coated with HABut, with a degree of substitution of 0.3 compared with the number of PMNs adhering to that coated with HA.

Example 18: Effect of Degree of Butyrate Substitution and Molecular Weight of Hyaluronic Acid on the Adhesion of Activated and Non-Activated PMFs Adhesion of PMNs stimulated with TNF to a surface coated with HA and HABut. HABut: sodium hyaluronate butyrate DS=0.3 Example no. 4; HABut samples no. 1: sodium hyaluronate butyrate DS=1.3 Example no. 7; HABut samples no. 2: HMW sodium hyaluronate butyrate DS=0.24 Example no. 8; HABut samples no. 3 HMW sodium hyaluronate butyrate DS=0.97 Example no. 10. Resting: negative control. PMA: positive control.

Black column: PMNs not activated with TNF. White column: PMNs activated with TNF.

The adhesion of the PMFs to the surfaces is evaluated as described in example 18.

Figure 4:
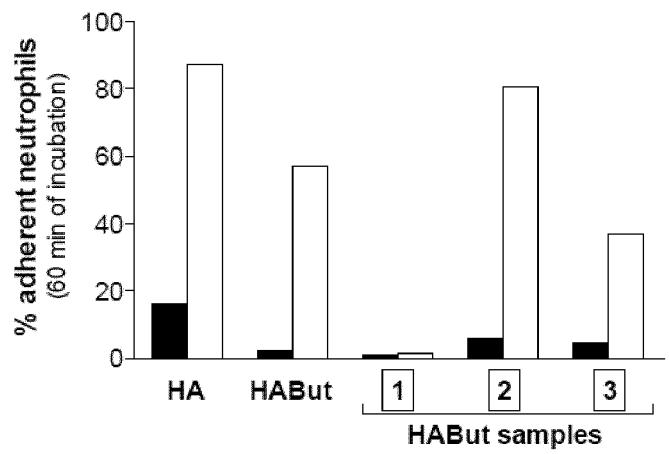
FIG. 4 shows hat when the degree of substitution with butyrate increases, HABut becomes a surface increasingly less permissive to adhesive interaction with PMNs.

The histogram reported in FIG. 4 shows that when the degree of substitution with butyrate increases, HABut becomes a surface increasingly less permissive to adhesive interaction with PMNs, whereas its molecular weight seems to be irrelevant.

The invention claimed is:

1. A process for the preparation of hyaluronic acid butyrate or a salt thereof, comprising reacting hyaluronic acid salified with sodium or another alkali metal in aqueous solution with butyryl-imidazolide in the presence of sodium carbonate.

2. The process according to claim 1 wherein the hyaluronic acid butyrate salt is sodium salt.

3. The process according to claim 2 wherein the hyaluronic acid sodium salt has a weight-average molecular weight ranging from $10^3$ to $10^6$ Daltons.

4. The process according to claim 1 wherein the hyaluronic acid butyrate has a substitution degree ranging from 0.01 to 2.5.

5. The process according to claim 4 wherein the hyaluronic acid butyrate has a substitution degree ranging from 0.1 to 2.

6. The process according to claim 1 wherein the reaction is carried out at a temperature ranging from 20° C. to 30° C.

7. The process according to claim 6 wherein the reaction is carried out at 25° C.

8. The process according to claim 7 wherein the reaction is carried out at a pH ranging from 9 to 11.

\* \* \* \* \*